United States Patent [19]

Faries, Jr. et al.

[11] Patent Number: 5,653,938

[45] Date of Patent: Aug. 5, 1997

[54] METHOD AND APPARATUS FOR ENSURING STERILITY OF SURGICAL DRAPES USED WITH SURGICAL EQUIPMENT

[75] Inventors: Durward Faries, Jr., McLean, Va.; Bruce R. Heymann, Silver Spring, Md.

[73] Assignee: O. R. Solutions, Inc., Chantilly, Va.

[21] Appl. No.: 427,938

[22] Filed: Apr. 26, 1995

[51] Int. Cl.⁶ .................... G05B 19/048; B01J 19/00
[52] U.S. Cl. .................... 422/3; 422/40; 422/105; 422/117; 422/119
[58] Field of Search .................... 422/3, 105, 117, 422/119, 40; 364/413.01, 807

[56] References Cited

U.S. PATENT DOCUMENTS

| | | | |
|---|---|---|---|
| 4,393,659 | 7/1983 | Keyes et al. | 62/66 |
| 4,474,016 | 10/1984 | Winchell | 62/60 |
| 4,934,152 | 6/1990 | Templeton | 62/66 |
| 5,040,699 | 8/1991 | Gangemi | 222/1 |
| 5,163,299 | 11/1992 | Faries, Jr. et al. | 62/66 |
| 5,310,524 | 5/1994 | Cambell et al. | 422/33 |
| 5,331,820 | 7/1994 | Faries et al. | 62/68 |
| 5,333,326 | 8/1994 | Faries et al. | 4/639 |
| 5,374,813 | 12/1994 | Shipp | 235/375 |
| 5,400,267 | 3/1995 | Denen et al. | 364/552 |
| 5,429,801 | 7/1995 | Faries, Jr. et al. | 422/41 |
| 5,443,082 | 8/1995 | Mewburn | 128/897 |
| 5,449,892 | 9/1995 | Yamada | 235/462 |
| 5,463,213 | 10/1995 | Honda | 235/468 |

*Primary Examiner*—Nina Bhat

[57] ABSTRACT

The sterility of a drape for use on surgical equipment is ensured by the use of bar codes and a microprocessor. When a drape containing a bar code is placed on the corresponding surgical equipment, a bar code reader ascertains the bar code on the drape. A microprocessor receives the bar code and determines whether the bar code has been previously written to memory indicating the drapes prior use. If the bar code is not present, the current bar code of the drape is written into memory, and subsequent operation of the surgical equipment commences. If the bar code is present, the microprocessor prevents the surgical equipment from operating. The microprocessor conserves memory by deleting bar code numbers of drapes that surpass a user determined time period.

28 Claims, 5 Drawing Sheets

METHOD AND APPARATUS FOR ENSURING STERILITY OF SURGICAL DRAPES USED WITH SURGICAL EQUIPMENT

BACKGROUND OF THE INVENTION

1. Technical Field

The present invention pertains to improvements in methods and apparatus for heating or cooling sterile surgical liquids and collecting surgical sterile slush. In particular, the invention is an improvement of the methods and apparatus disclosed in U.S. Pat. No. 4,393,659 (Keyes et al), U.S. Pat. No. 4,934,152 (Templeton), U.S. Pat. No. 5,163,299 (Faries, Jr. et al), U.S. Pat. No. 5,331,280 (Faries, Jr. et al), U.S. Pat. No. 5,333,326 (Faries, Jr. et al), and U.S. patent application Ser. No. 08/326,423, filed Oct. 20, 1994, now U.S. Pat. No. 5,457,962(Faries, Jr. et al. The disclosures in those patents and applications are expressly incorporated by reference herein in their entireties.

2. Discussion of the Prior Art

The above-referenced Keyes et al patent discloses a surgical slush producing system having a cabinet with a heat transfer basin at its top surface. A refrigeration mechanism in the cabinet takes the form of a closed refrigeration loop including: an evaporator in heat exchange relation to the outside surface of the heat transfer basin; a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton patent, the Keyes et al system has a number of disadvantages. In particular, the separate product basin must be removed and re-sterilized after each use. Additionally, the glycol or other thermal transfer medium is highly flammable or toxic and, in any event, complicates the procedure. The Templeton patent discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush.

The Faries, Jr. et al U.S. Pat. No. (5,163,299) notes that scraping congealed liquid from the drape is undesirable in view of the potential for damage to the drape, resulting in a compromise of sterile conditions. As a solution to the problem, the patent proposes that the drape be lifted or otherwise manipulated by hand to break up the congealed liquid adhering to the drape. Although this hand manipulation is somewhat effective, it is not optimal, and often is inconvenient and constitute an additional chore for operating room personnel.

The Faries, Jr. et al U.S. Pat. No. (5,331,820) resolves the problem of manual manipulation of the drape by providing a method and apparatus to automatically remove the congealed liquid adhering to the drape without endangering the integrity of the drape. A flat disk or plate is provided at the bottom of the basin under the drape. The plate is moved in an up and down matter to disengage the congealed liquid from the drape. The plate may be attached to a mechanism below the basin, or to the drape itself as disclosed in copending U.S. patent application 08/336,423.

Templeton further provides an electrical heater disposed at the bottom of the basin to convert the sterile slush to warmed liquid, or to heat additional sterile liquid added to the basin. Templeton describes the need for such warm sterile liquid as occurring after a surgical procedure is completed to facilitate raising the body cavity of the surgery patient back to its normal temperature by contact with the warmed liquid. However, there are a number of instances during a surgical procedure when it is desirable to have simultaneous access to both the sterile warmed liquid and the sterile surgical slush. The Faries, Jr. et al U.S. Pat. No. (5,333,326) patent provides a method and apparatus for simultaneously providing separate surgical slush and warmed surgical liquid during a surgical procedure using a single drape for such a unit.

The foregoing patents do not provide a way to ensure sterile conditions by restricting the use of a surgical drape to only one surgical procedure. Specifically, once a drape has been used to contain warmed, chilled or frozen sterile media during one surgical procedure, it is no longer sterile for such use in another surgical procedure. Since drapes are typically not capable of withstanding autoclaving, and since other re-sterilization procedures are largely impractical for drapes, it is important that a fresh sterile drape be used for each procedure. Although operating room personnel can be advised and cautioned about the importance of discarding a drape after a procedure, there is no assurance that carelessness will not result in re-use of a drape and thereby compromise the sterile field of an entire surgical procedure.

OBJECTS AND SUMMARY OF THE INVENTION

Accordingly, it is an object of the present invention to provide an apparatus and method to automatically ensure the sterility of a drape used to contain sterile fluid by determining whether a surgical drape has been previously used.

According to the present invention, each surgical drape contains automatically detectable indicia identifying the individual drape. When the drape is positioned onto the corresponding apparatus for containing and thermally treating sterile liquids, a code reader embedded in the apparatus scans the indicia to ascertain the drape's identification code. The identification code is then sent to a microprocessor to determine if that identification code matches identification codes stored in memory of surgical drapes that have been previously used. If the microprocessor determines that the identification code of the current drape matches the identification code in memory of a previously used drape, the microprocessor prevents the operation of the apparatus. If the microprocessor does not find a match, the identification code of the current drape is written into memory, and the operation of the apparatus commences. In order to conserve memory, the microprocessor deletes all memory entries that surpass a predetermined length of time. Alternately, the microprocessor may maintain a large queue of identification codes of drapes previously used, and when the queue becomes full, delete the oldest entries in the queue as new entries are added.

The above and still further objects, features and advantages of the present invention will be apparent upon consideration of the following detailed description of the specific embodiments thereof, particularly when taken in conjunction with the accompanying drawings wherein like components are designed by like reference numerals.

DESCRIPTION OF THE PREFERRED EMBODIMENT

The present invention can be applied to various apparatus for providing thermally treated sterile media such as surgical slush machines, liquid warming and cooling systems, and multiple unit machines capable of performing both liquid warming, cooling and slush generation.

Figure 1:
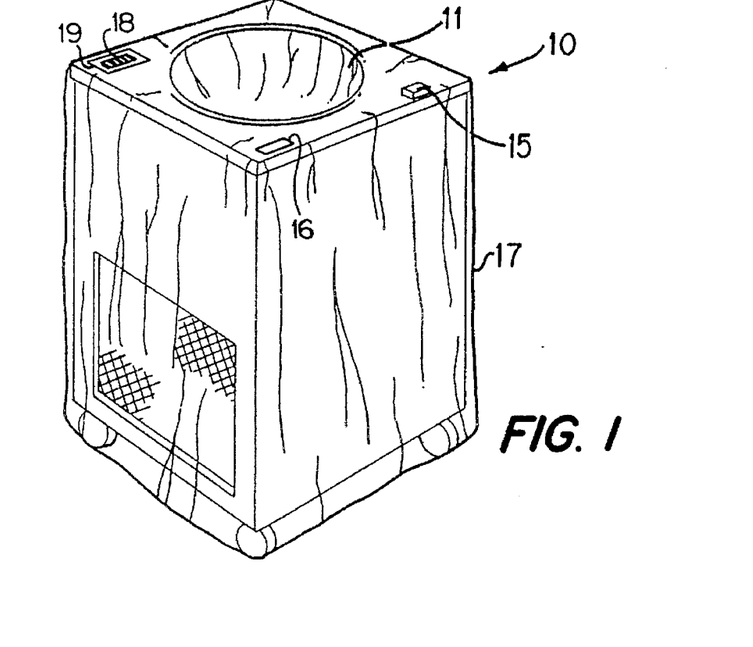
FIG. 1 is a view in perspective of a surgical slush machine and surgical drape according to the present invention.

FIG. 1 illustrates an example of a surgical slush machine including a surgical drape implementing the sterility determination of the present invention. The surgical slush machine includes a cabinet 10 with a top surface having a basin 11 mounted thereon in an appropriately sized recess. Basin 11 is made of thermally conductive material, typically stainless steel, and includes a generally flat bottom wall and a frusto-conical sidewall. A conventional refrigeration unit (not shown) is disposed within cabinet 10 and typically includes a compressor, a condenser and an expansion control unit connected by appropriate fluid conduits in a closed refrigeration loop with an evaporator (not shown). The evaporator is in the form of a coil wound about the exterior surface of basin 11 in thermal transfer relation therewith. When the refrigeration unit is activated by means of appropriate controls 15 and temperature control 16, the evaporator cools the sidewall of basin 11 to a temperature substantially below the freezing temperature of the liquid used in forming the sterile slush. A sterile surgical drape 17, preferably transparent, is disposed over the top and sides of cabinet 10 and made to conform to the side wall and bottom of basin 11.

The portion of surgical drape 17 disposed in the basin serves as a sterile receptacle for sterile liquid placed therein to be frozen into the described sterile slush. Drape 17 contains a bar code 18 positioned in or over a bar code reader socket or window 19 in order for the bar code to be read and the drape checked for sterility in order to control electrical power application to temperature controller 16. The bar code is permanently affixed to, or imprinted on the drape in any suitable manner, typically at the time the drape is manufactured.

Figure 2:
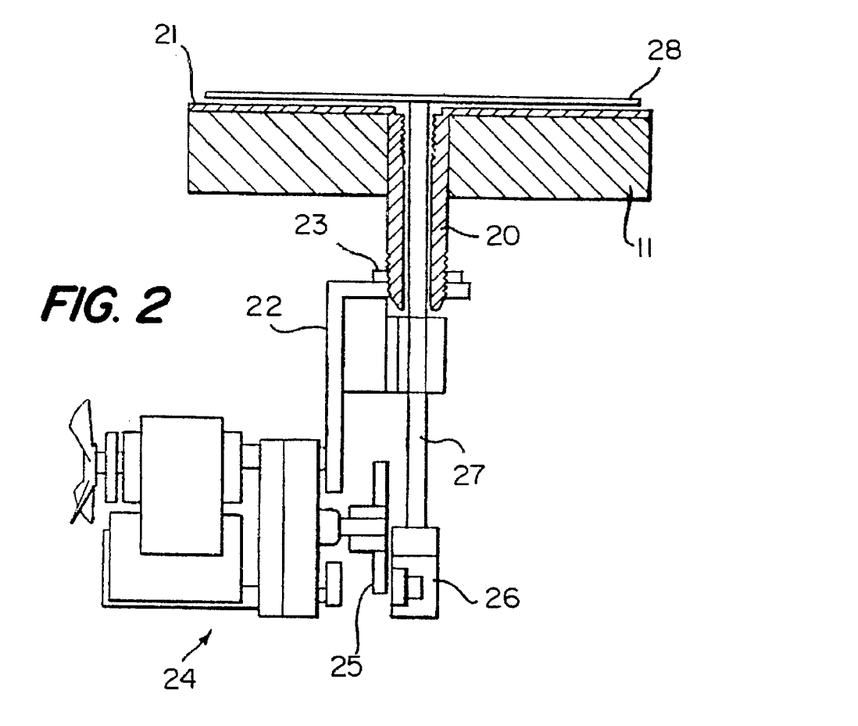
FIG. 2 is a view in elevation and partial section of a mechanism to remove slush from the surgical drape of FIG. 1.

When the surgical slush machine is operating, the sterile liquid in the drape receptacle freezes in pieces on the surgical drape covering the sidewalls of the basin. FIG. 2 depicts a mechanism for automatically removing the frozen pieces from the surgical drape covering the walls of the basin to form the sterile slush. Specifically, the bottom of basin 11 is provided with a central hole through which an adapter tube 20 extends. Adapter tube 20 has an annular flange 21 extending radially outward from the upper end of the tube and positioned to rest on the bottom wall of the basin between the basin and the drape container (not shown). The bottom end of adapter tube 20 is externally threaded and is engaged by a support bracket 22 and lock washer 23 such that bracket 22 is suspended interiorly of the machine cabinet 10 (FIG. 1). A gear motor assembly, generally designated at 24, is supported by bracket 22 and includes a rotor 25 operatively engaged with a bearing track 26. A drive shaft 27 has its bottom end operatively engaged to bearing track 26 to cause the shaft to reciprocate longitudinally as rotor 25 rotates. Shaft 27 extends upwardly through adapter tube 20 and has its upper end secured to the center of the underside of a plate 28 disposed between the adapter tube flange 21 and the bottom of the drape receptacle (not shown). Accordingly, as motor 24 reciprocates shaft 27 up and down, the shaft moves plate 28 up and down. The plate in turn moves the bottom of the drape container up and down to loosen attached pieces of frozen saline.

Figure 3:
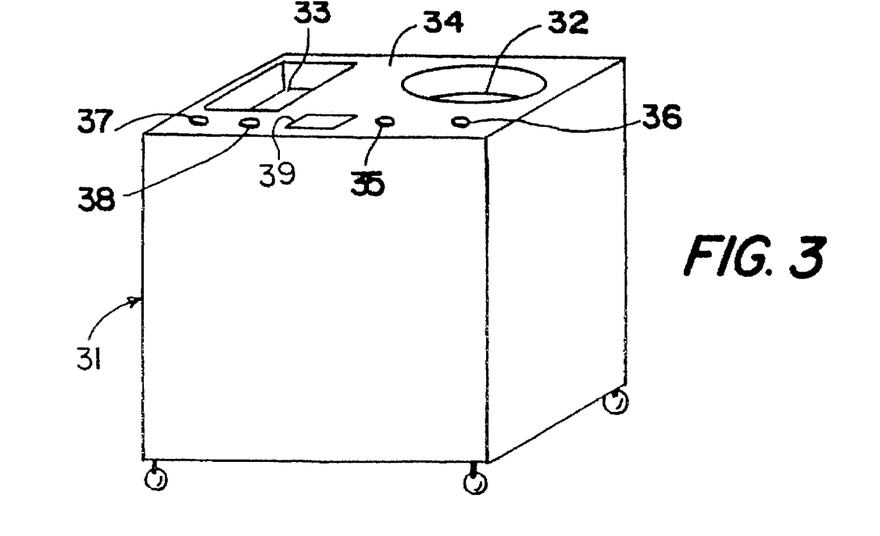
FIG. 3 is a view in perspective of a machine containing both a heating basin and a cooling basin for use with the drape of the present invention.

Referring to FIG. 3, there is illustrated an example of apparatus containing both a slush generating unit and a sterile liquid warming unit. An integral assembly 31 includes a cooling basin 32 for slush and a warming basin 33 for liquid recessed into the top surface 34 of a common cabinet. Also disposed on top surface 34 are cooling unit power switch 35, a cooling unit temperature controller/indicator 36, a heater power switch 37, a heater unit temperature controller/indicator 38, and a bar code reader socket or window 39.

Figure 4:
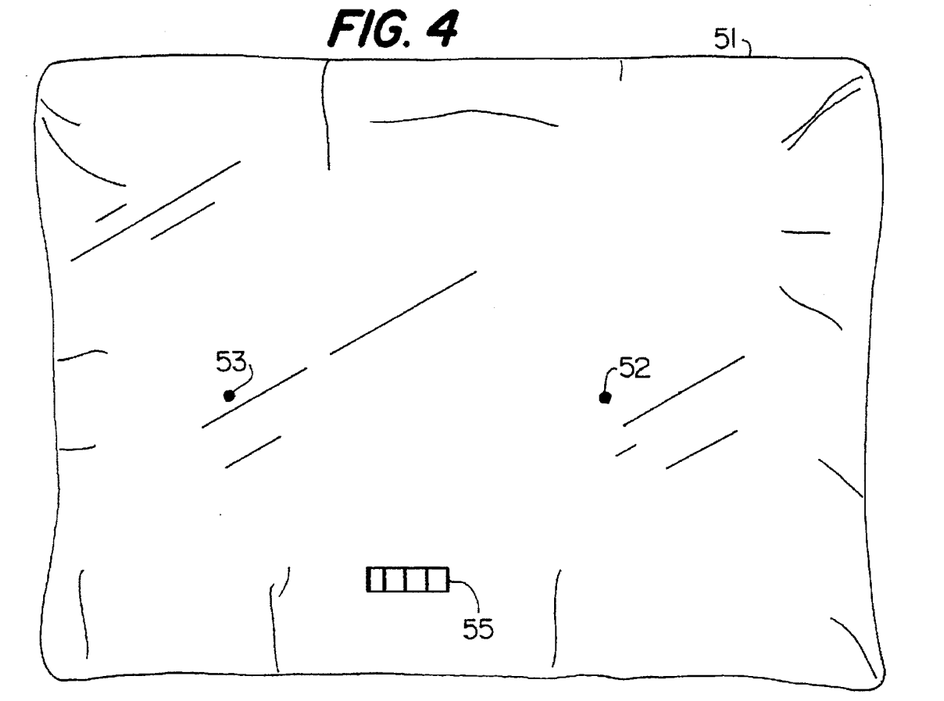
FIG. 4 is a view in plan of a surgical drape of the present invention having particular utility with the machine of FIG. 3.

A sterile surgical drape 51 suitable for covering the entire top surface 34 and to provide drape receptacles for both basins 32 and 33, is illustrated in FIG. 4. Drape 51 has bar code 55 affixed, imprinted or otherwise attached thereto for use in determining sterility of the drape. Drape 51 has two centering marks or indicia 52, 53 adapted to be placed over the centers of the cooling and heating basins 32 and 33, respectively, during installation of the drape.

Figure 5:
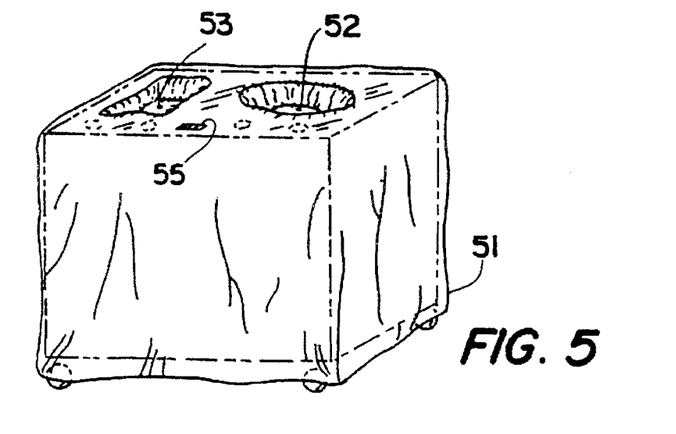
FIG. 5 is a view in perspective of the surgical drape of FIG. 4 deployed on the machine of FIG. 3.

FIG. 5 illustrates the centering indicia 52, 53 are properly positioned when drape 51 is pushed down into respective basins until the drape conforms to the basin shapes. Bar code 55 is positioned over bar code reader socket or window 39 (FIG. 3) to determine the drape's sterility.

Figure 6:
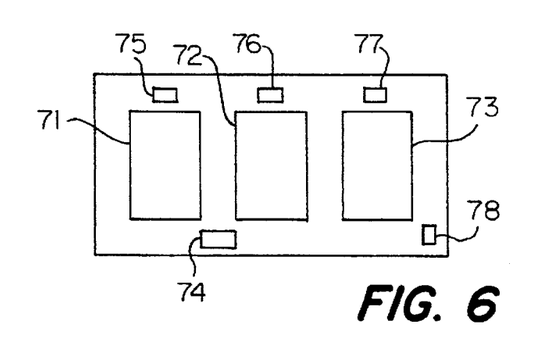
FIG. 6 is a top view in plan of a machine that simultaneously produces warm sterile liquid, chilled sterile liquid and sterile slush.
Figure 7:
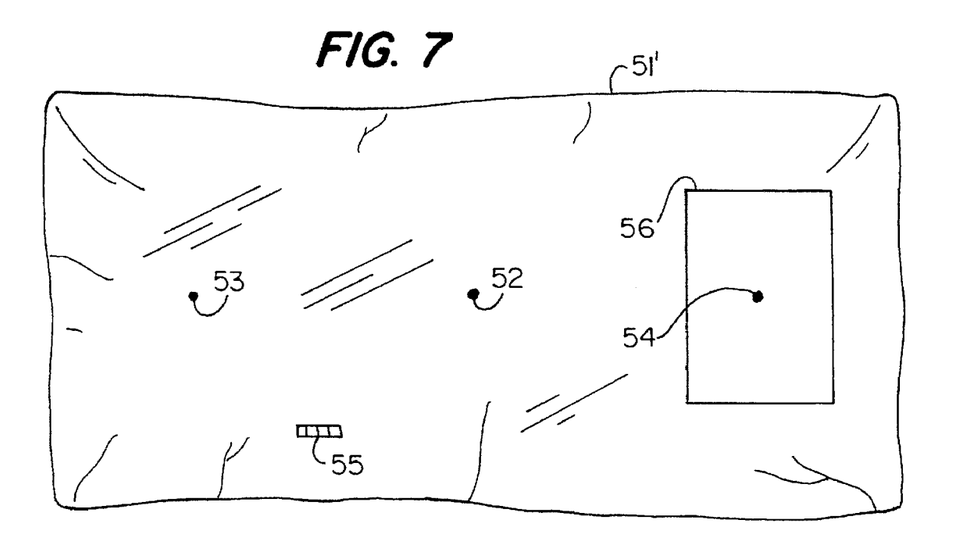
FIG. 7 is a view in plan of a surgical drape for use with the machine of FIG. 6.

Other surgical equipment and drapes can be utilized by positioning or connecting heating, cooling and surgical slush units together, while utilizing a single drape capable of encompassing all the units as shown in FIG. 6. For example, a common unit contains cooler basin 71 for cooling sterile liquid, warmer basin 72 for providing heated liquid, and surgical slush generating basin 73 for providing sterile slush. The basins are generally similar to the basins previously described herein and in the disclosures incorporated by reference. Temperature indicators/controllers 75, 76, 77 monitor and control the temperature for their respective basins. Power switch 78 enables operation of the unit. Bar code reader socket or window 74 is provided to read the bar code of the surgical drape. The surgical drape 51' for such a unit is illustrated in FIG. 7. As shown, surgical drape 51' has three sensor marks 52, 53, 54 which are to be positioned in the centers of the corresponding basins 71, 72, 73. Bar code 55 is to be positioned over bar code reader socket or window 74 to enable the drape bar code to be read. Surgical drape 51' further contains a disk or plate 56 which is used for automatic slush separation from the surgical drape. Plate 28 of FIG. 2 corresponds to plate 56 of FIG. 7, but instead of the plate being part of the machine, the plate is attached to the drape and removably connected to the removal mechanism when the surgical drape is installed.

The surgical drapes for all of the above machines are made of material that is impervious to the heated and cooled liquid and slush, and is sufficiently soft and flexible to conform to the walls of basins. Typically, by way of example only, the surgical drape is made of materials commonly used in hospitals for surgical drapes. The drapes may also be made of polyurethane film as disclosed for the surgical drape in the aforementioned Templeton patent. The surgical drapes are designed to be disposable after a single use and are provided pre-sterilized and pre-packaged in a leakproof plastic bag or other sealed container to preserve the sterile nature of the surgical drape during storage.

Figure 8:
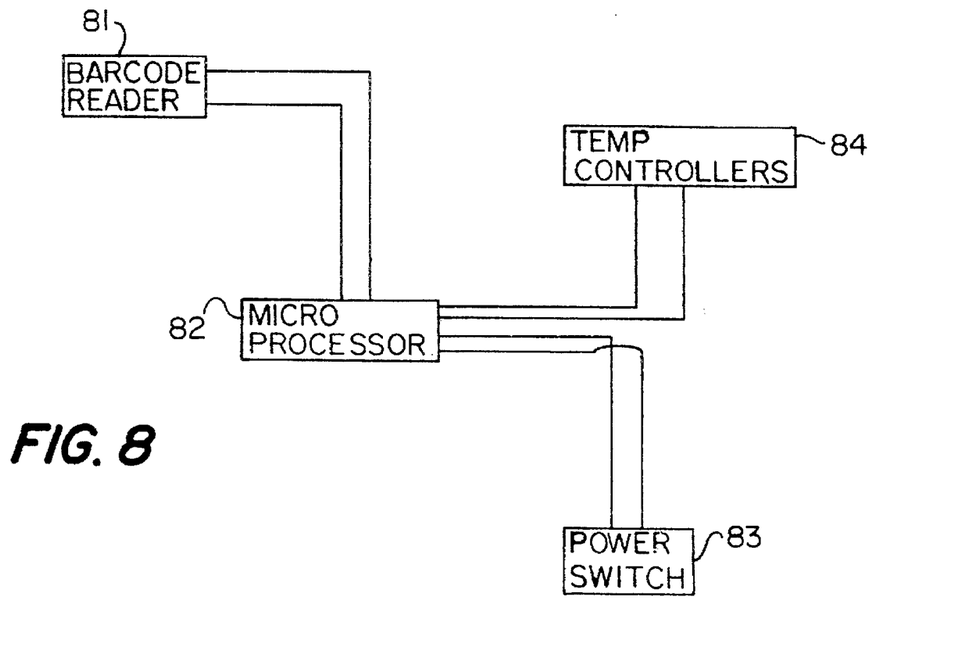
FIG. 8 is a schematic illustration of a sterile drape determination circuit according to the present invention.

Referring to FIG. 8, a sterile drape determination circuit is embodied in each of the various machines described above. The bar code reader is disposed beneath the bar code reader window or inserted into the bar code reader socket. The output signals from the microprocessor are connected to the various temperature controllers/indicators. The sterile drape determination circuit comprises a conventional bar code reader 81 which reads or senses the bar code 55 from the surgical drape. A microprocessor 82 compares the sensed bar code to previously used surgical drape bar codes stored in the microprocessor memory to determine if that bar code has been previously sensed, indicating that the surgical drape has already been used. The microprocessor controls various temperature controllers 84 of respective warming, cooling and slush generation units, and is also connected to power switch 83. Operation of the sterility circuit is described immediately below with reference to FIG. 9.

Figure 9:
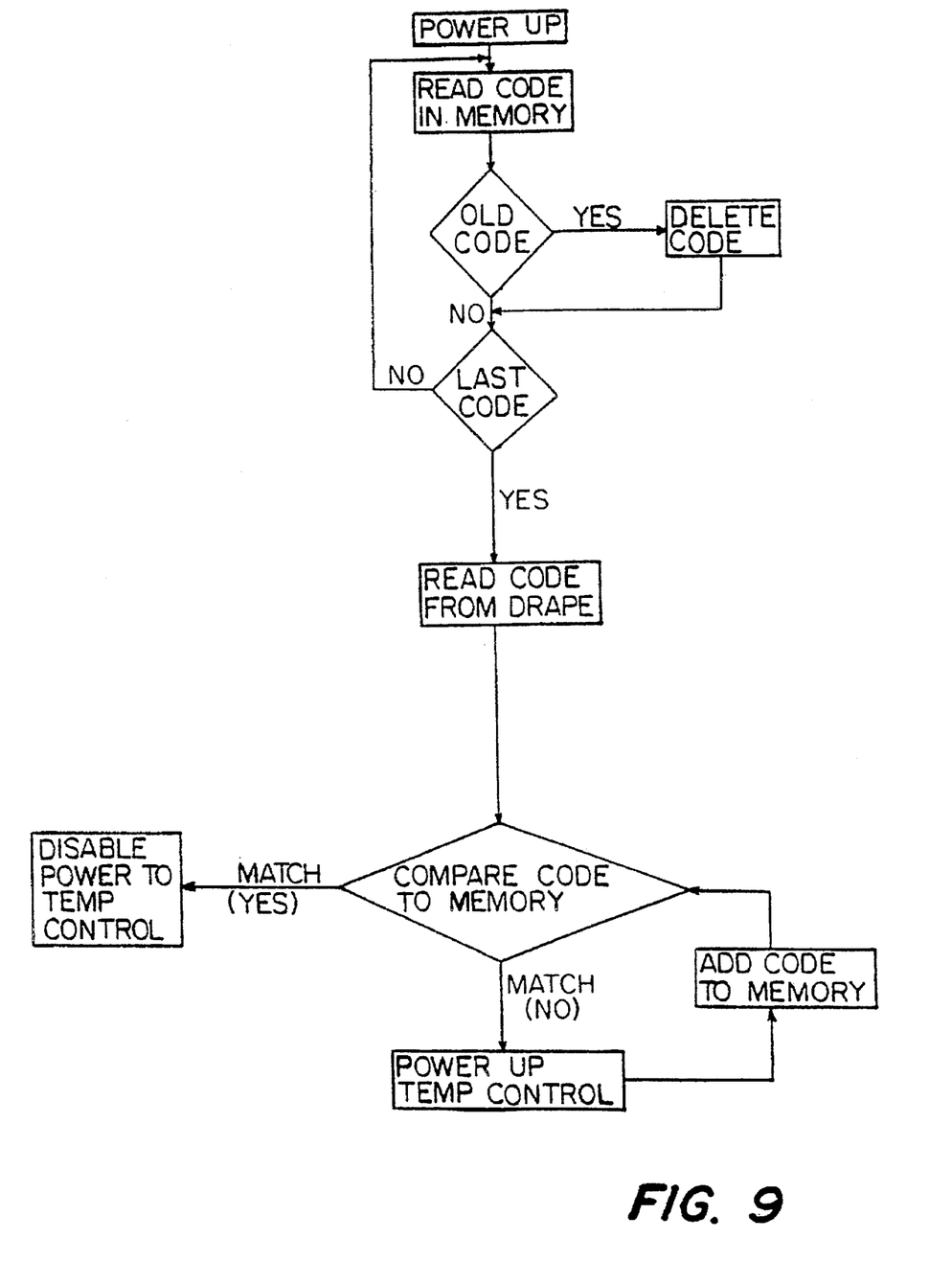
FIG. 9 is a flowchart of the operation of a sterile drape determination circuit.

On power up of the machine, the microprocessor conserves memory by deleting older stored bar codes of previously used drapes which have been in storage longer than a predetermined time period. Next, the bar code reader ascertains the bar code of the surgical drape currently being used. The ascertained bar code is sent to the microprocessor to determine if the current surgical drape bar code resides in memory indicating that the surgical drape has been previously used and is therefore not sterile. If there is no match, the microprocessor adds the current surgical drape bar code to memory and enables the temperature controllers to operate their respective temperature control units. If a match was found, then the surgical drape is deemed non-sterile because of prior use and the microprocessor disables power to the temperature controllers to prevent operation with a non-sterile drape.

Microprocessor control is accomplished by software providing the data comparisons and old data deletions. The microprocessor can be implemented by virtually all commercially available microprocessor chips as known in the art.

It will be appreciated that the embodiments described above and illustrated in the drawings represent only a few of the many ways of implementing assured sterility of a surgical drape in the present invention.

The function of the microprocessor of the present invention is capable of being accomplished by a memory in conjunction with general circuitry or combinational logic to perform the comparisons. Memory equivalents include conventional semiconductor memories, optical memories, or any other storage devices capable of storing identification codes.

The present invention is capable of including sound or visual indicators notifying when a drape is in a non-sterile condition. Such indicators include an alarm, buzzer, colored light, speech synthesizer or any other indicator used for specifying a condition or state of an object.

The memory conservation by deletion of old data may be alternatively accomplished by use of a queue. Entries are added to the queue until the queue becomes full. After the queue becomes full, the oldest entries are removed as new entries are added. The queue may be implemented by software, or may be realized in hardware.

The present invention alternatively may be implemented by controlling power to a machine based on whether indicia on the drape are sensed. The drape is positioned on the machine with the indicia located adjacent a window or reader socket. A reader beneath the window or placed in the socket sends a signal to the microprocessor indicating whether or not indicia are present. The microprocessor then controls power to the machine based on the signal. An embodiment for this configuration is substantially similar to the ones described above, eliminating the feature of comparing the sensed indicia with previously stored indicia. The indicia utilized may be magnetic, optical, bar code or any other indicia capable of automatic recognition and, unlike the embodiments described above, the indicia on every drape may be identical. The microprocessor may be replaced with general circuitry, combinational logic or any other switching means capable of controlling power to a device.

Although the preferred embodiment discloses a bar code as the coded indicia on the drape, the present invention is not limited to that embodiment. Any number of identification codes or tags and associated devices for reading such codes or tags may be implemented according to the present invention. Such schemes include any optically sensed codes or tags whether or not they are visible to a user (bar codes and readers, character recognition, etc.) magnetic codes or tags, voice recognition devices, and any other means of uniquely tagging and identifying objects.

From the foregoing description it will be appreciated that the invention makes available a novel method and apparatus for ensuring sterility of a drape used for a machine for containing and thermally treating sterile liquid by comparing the drape's identification code to identification codes of drape's that have been previously used and stored. In addition, the invention prevents operation of the machine if a non-sterile drape is being used.

Having described preferred embodiments of a new and improved method and apparatus for ensuring sterility of surgical drapes for use with surgical equipment, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. In a machine for thermally treating a sterile fluid medium in a drape container to permit use of fluid medium in a surgical procedure, a method for preventing re-use of non-sterile drapes comprising the steps of:
   (a) permanently placing on each drape coded indicia uniquely identifying said each drape;
   (b) positioning one of said drapes on said machine, prior to each thermal treatment of sterile fluid, to form said drape container and to place said coded indicia adjacent a reading device;
   (c) reading said coded indicia from the positioned drape;
   (d) detecting sterility of the positioned drape by comparing said coded indicia of the positioned drape to coded indicia stored in a memory, wherein said coded indicia stored in said memory identify non-sterile previously used drapes; and
   (e) controlling power to a temperature controller of said machine based on said comparison such that said machine is disabled in response to detecting a non-sterile drape.

2. The method according to claim 1 further comprising the step of:
   (f) deleting from said memory stored coded indicia that have been stored longer than a predetermined time period.

3. The method of claim 1 wherein said step (e) comprises disabling power to said temperature controller when said coded indicia of said positioned drape matches a coded indicia in said memory.

4. The method of claim 3 wherein said step (e) further comprises storing said coded indicia of said positioned drape in said memory and enabling power to said temperature controller when said coded indicia of said positioned drape does not match any coded indicia in said memory.

5. The method of claim 1 wherein said step (a) comprises permanently placing on each drape an optically sensed coded indicia uniquely identifying each said drape.

6. The method of claim 1 wherein said step (a) comprises permanently placing on each drape a bar code uniquely identifying each said drape.

7. A method for preventing use of unsuitable surgical drapes with a thermal treatment machine of the type having a basin into which a portion of a surgical drape is placed to conform to the basin and receive sterile liquid to be used during a surgical procedure and temperature controlled by controlling the temperature of the basin, said method comprising the steps of:
   (a) physically placing an indicator on suitable drapes;
   (b) detecting in said machine the presence of said indicator for a drape placed on said machine; and
   (c) enabling temperature control of said basin only in response to detection of said indicator for said drape placed on said machine.

8. The method of claim 7 wherein step (a) includes disposing indicia on said suitable drapes; and wherein step (b) includes detecting the presence of said indicia.

9. The method of claim 8 wherein the indicia are optically detectable.

10. The method of claim 8 wherein the indicia are magnetic and are magnetically detectable.

11. The method of claim 7 wherein step (a) includes disposing coded indicia on said suitable drapes to uniquely identify suitable drapes and to distinguish each suitable drape from all other suitable drapes, and wherein step (b) includes reading said coded indicia; and further comprising the steps of:
   (d) storing coded indicia that have been read from suitable drapes previously used with the system;
   (e) comparing coded indicia being read in step (b) with all coded indicia stored in step (d) to determine match and non-match conditions between the coding indicia being read and each of the stored coded indicia; and
   (f) inhibiting the enabling of temperature control in step (c) unless said non-match condition is detected.

12. An apparatus for detecting a sterility of a surgical drape comprising:
   thermal treatment means for thermally treating a liquid, said means including at least one basin;
   a surgical drape covering and substantially conforming to said at least one basin to serve as a drape container for said liquid, said surgical drape including an identification code;
   reader means for reading said identification code of said surgical drape when said surgical drape is properly positioned on said thermal treatment means;
   actuable means for operating said thermal treatment means to control a temperature of each said basin;
   memory means for storing said identification codes read by said reader means, wherein said codes identify non-sterile previously used drapes;
   comparing means for detecting the sterility of said surgical drape by comparing said identification code of said surgical drape to identification codes stored in said memory means; and
   control means for controlling said thermal treatment means based on said comparison such that said thermal treatment means is disabled in response to said comparing means detecting a non-sterile drape.

13. The apparatus of claim 12 further comprising means for deleting from said memory means stored identification codes that have been stored for longer than predetermined time period.

14. The apparatus of claim 12 wherein said thermal treatment means further includes means for generating surgical slush in said drape container.

15. The apparatus of claim 14 wherein said surgical drape further comprises a movable plate for automatically removing surgical slush formed on said surgical drape.

16. The apparatus of claim 12 wherein said thermal treatment means includes means for generating a heated liquid in said drape container.

17. The apparatus of claim 12 wherein said thermal treatment means comprises at least two basins and further includes means for generating heated and cooled liquid simultaneously in separate basins.

18. The apparatus of claim 12 wherein said control means disables power to said thermal treatment means when said identification code of said surgical drape matches an identification code in said memory means.

19. The apparatus of claim 18 wherein:
   said comparing means further includes means for storing said identification code of said surgical drape in said memory means; and
   said control means further includes means for enabling power to said actuable means when said identification code of said surgical drape does not match any identification codes stored in said memory means.

20. The apparatus of claim 12 wherein said identification code of said surgical drape comprises an optically sensed identification code.

21. The apparatus of claim 12 wherein said identification code of said surgical drape comprises a bar code and said reader means comprises a bar code reader.

22. A device for use in a surgical apparatus to ensure sterility of liquid being temperature controlled, wherein said apparatus includes at least one temperature controlled basin and reader means fixedly positioned relative to said apparatus, and said device comprises a drape containing coded indicia adapted and disposed to be read by said reader means for automatic identification of said drape by said apparatus when said drape is placed on said apparatus such that said indicia are positioned over said reader means and a portion of said drape is disposed in said at least one basin to form a drape container in the basin for containing and maintaining said liquid, wherein said coded indicia indicate the sterility condition of said drape, and said apparatus includes means for disabling operation of said apparatus in response to identifying a non-sterile drape thereby preventing operation of said apparatus with a non-sterile drape container.

23. The device of claim 22 wherein said coded indicia comprises optically sensed coded indicia.

24. The device of claim 22 wherein said coded indicia comprises a bar code.

25. An apparatus for detecting a sterility, comprising:
   thermal treatment means for thermally treating a liquid, said thermal treatment means including at least one basin;
   a surgical drape covering and substantially conforming to said at least one basin to serve as a drape container for said liquid, said surgical drape including an identification code indicating sterility of said drape;
   reader means for detecting sterility of said drape by sensing said identification code of said surgical drape when said surgical drape is properly positioned on said thermal treatment means;
   actuable means for operating said thermal treatment means to control a temperature of each said basin; and
   power control means for disabling power to said thermal treatment means when said reader means does not sense an identification code of said surgical drape.

26. Apparatus for preventing use of unsuitable surgical drapes with a thermal treatment machine of the type having a basin into which a portion of a surgical drape is placed to conform to the basin and receive sterile liquid that is to be used during a surgical procedure and temperature controlled by controlling the temperature of the basin, said apparatus comprising:
   drape, indicator means for designating suitable drapes for use with said machine;
   detector means fixedly positioned on said machine for detecting the presence of said indicator means for a drape placed on said machine; and
   control means for enabling temperature control of said basin only in response to detection of indicator means for said drape placed on said machine.

27. The apparatus of claim 26 wherein said indicator means comprises coded indicia disposed on said suitable drapes, and wherein said detector means comprises means for detecting said coded indicia.

28. The apparatus of claim 26 wherein said drape indicator means comprises coding means uniquely identifying suitable drapes and distinguishing each suitable drape from all other suitable drapes with said coded indicia;
   wherein said detector means comprises code reading means for reading said coded indicia;
   and further comprising:
      memory means for storing coded indicia previously read by said code reading means;
      comparison means for comparing coded indicia being read by said code reading means with all coded indicia stored in said memory means to determine match and non-match conditions between the coded indicia being read and each of said stored coded indicia; and
      means for inhibiting said control means from enabling temperature control of said basin in response to detection of a match condition by said comparison means.

* * * * *